United States Patent [19]

Mörsdorf et al.

[11] Patent Number: 5,182,294
[45] Date of Patent: Jan. 26, 1993

[54] IMIDAZOLYL PROPYL GUANIDINE DERIVATIVE AND A PHARMACEUTICAL COMPOSITION CONTAINING THIS COMPOUND

[75] Inventors: Peter Mörsdorf, Langenzenn; Heidrun Engler, Cadolzburg; Helmut Schickaneder, Eckental; Kurt-Henning Ahrens, Nuremberg, all of Fed. Rep. of Germany

[73] Assignee: Heumann Pharma GmbH & Co., Nuremberg, Fed. Rep. of Germany

[21] Appl. No.: 639,511

[22] Filed: Jan. 10, 1991

[30] Foreign Application Priority Data

Jan. 15, 1990 [EP] European Pat. Off. ...... 90/100726.0

[51] Int. Cl.⁵ .................. A61K 31/44; C07D 401/12
[52] U.S. Cl. ............................. 514/341; 546/278
[58] Field of Search ................... 546/278; 514/341

[56] References Cited

U.S. PATENT DOCUMENTS 4,948,802 8/1990 Mörsdorf et al. ............ 546/278
5,021,431 6/1991 Buschauer et al. ............ 546/278

Primary Examiner—Jane T. Fan
Attorney, Agent, or Firm—Burns, Doane, Swecker & Mathis

[57] ABSTRACT

A new imidazolyl propyl guanidine derivative corresponding to formula I

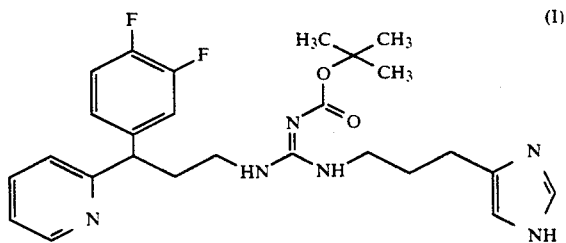

is described, which is distinguished by a combination of particularly advantageous properties for the treatment of diseases of the heart and circulation.

6 Claims, No Drawings

IMIDAZOLYL PROPYL GUANIDINE DERIVATIVE AND A PHARMACEUTICAL COMPOSITION CONTAINING THIS COMPOUND

Cardiac insufficiency is a widespread clinical syndrome, especially in industrial countries. It is characterised by the incapacity of the heart to provide the output required by the organism. Digitalis glycosides and β-sympathomimetic drugs have for many decades been the two most important groups of pharmaceutical substances used for the medical treatment of cardiac insufficiency but their numerous disadvantages have in recent years led to an intensive search for new classes of active compounds for the treatment of cardiac insufficiency. In the course of this work, potent cardiotonic substances have been found both in the group of phosphodiesterase-III-inhibitors and among the histamine-$H_2$ agonists.

DE-OS 35 12 084, 35 28 214, 35 28 215 and 36 31 334 and EP-OS 0 199 845 describe histamine-$H_2$ agonists in which on the one hand the potency of the compounds has been able to be considerably increased compared with that of impromidine (G. J. Durant et al, Nature (London), 1978, 276, 403) and on the other hand the undesirable side effects of impromidine could be removed by the incorporation of additional $H_1$-antagonistic units. These compounds are, however, like impromidine, insufficiently active or completely inactive when administered orally although they have an excellent cardiotonic action when applied parenterally.

Guanidine carboxylic acid esters corresponding to the following general formula

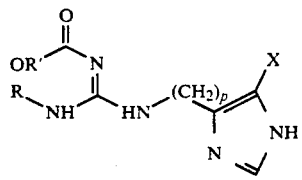

wherein R, R' and X stand for certain groups and p has the value 2 or 3 are described in DE-OS 37 26 381.

As described in DE-OS 37 26 381, the compounds corresponding to the above formula have a very favourable effect in increasing the contractility of the heart and at the same time are much more readily available orally. The oral availability is higher by a factor of about 20 than that of guanidine derivatives not substituted with an ester group, which are described in the above-mentioned German and European Offenlegungsschriften, but they have insufficient parenteral, e.g. intravenous availability.

It has now been found that a particular compound which conforms to the general formula of the compounds described and claimed in German Offenlegungsschrift DE-OS 37 26 381 but is not specifically described therein has special, unforeseeable advantages. This compound has a combination of particularly advantageous properties for the treatment of diseases of the heart and circulation.

The present invention therefore relates to the compound $N^1$-[3-(3,4-difluorophenyl)-3(2-pyridyl)-propyl]$N^2$-tert.-butoxycarbonyl-$N^3$-[3-(1H-imidazol-4-yl)propyl]guanidine corresponding to formula I

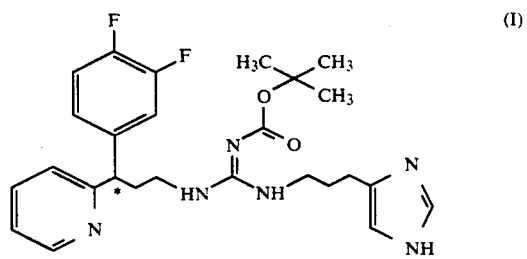

and to its physiologically acceptable salts and solvates. The compound corresponding to formula I may be present in various tautomeric forms as represented by formulae Ia–If and in two enantiomeric forms as regards the optically active carbon atom C*. The present invention therefore also relates to the enantiomeric and tautomeric derivatives of the compound of formula I.

The compound of formula I is characterised pharmacologically by a dual action profile in which it has a powerful histamine-$H_2$-agonistic action combined with an $H_1$-antagonistic action. The combination of these two properties is particularly advantageous for the treatment of diseases of the heart and circulation since on the one hand the powerful $H_2$-agonistic activity produces a good positive inotropic effect and on the other hand the $H_1$-antagonistic component prevents harmful side effects such as, for example, coronary spasms.

Compared with the compounds specifically described in DE-OS 37 26 381, the compound according to the invention corresponding to formula I has two important advantages. In vivo experiments with guinea-pigs have shown that the compound of formula I has an excellent positive inotropic action not only when administered orally but also when administered parenterally, e.g. by intravenous infusion (Table I).

This enables the compound to be used both in emergency medicine for the treatment of acute cardiac insufficiency and for long-term oral therapy of chronic cardiac insufficiency.

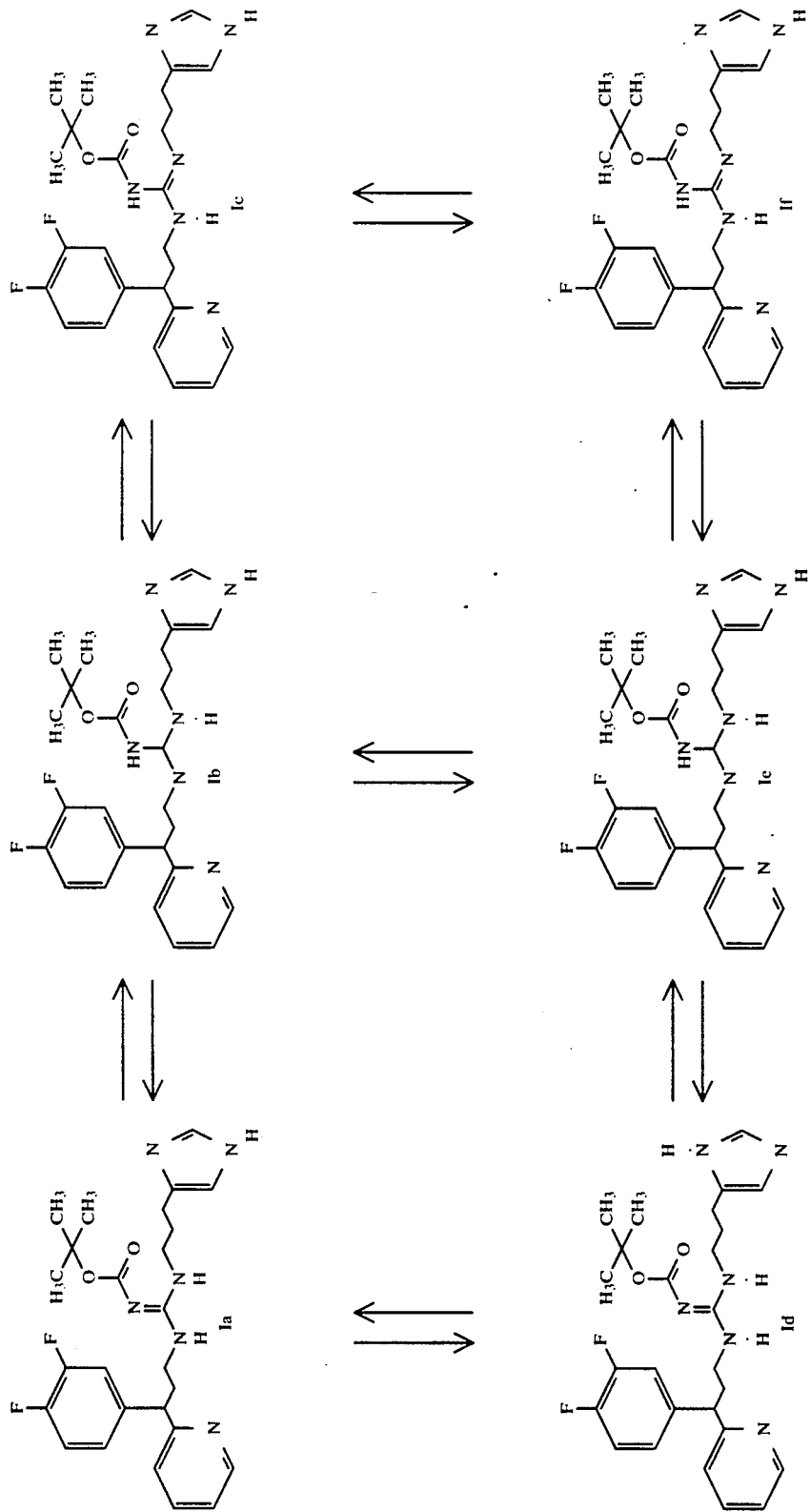

HAEMODYNAMIC CHARACTERISATION ON NARCOTISED guinea-pigs

Method

The animals are narcotised with urethane (1.5 g/kg). The trachea is cannulated for volume controlled breathing. The two carotids are then exposed operatively. A TIP catheter.(3F) is introduced through the right carotid and then moved forwards through the ascending aorta into the left ventricle while the pressure is continuously recorded. Successful passage through the aortic valves is recognised by the typical left ventricular pressure curve. A thermistor probe (3F, F. Edwards) is pushed forward into the aortic arch through the left carotid for thermodilution. The thermistor probe has a lumen for recording the arterial blood pressure. A catheter is passed through the right jugular vein to be placed in front of the right atrium for applying the cold injection (0.2 ml of 0.9% NaCl, 15° C.). The test substances are applied after haemodynamic stabilization and with $\beta$-blockage (Metoprolol 2 mg/kg i.m.). All the circulatory parameters are continuously recorded on a direct writing instrument. The contractility (dp/dt) is calculated from the volume curve.

For intravenous application, the test substances are dissolved in physiological saline solution and infused through the left jugular vein (infusion volume 0.02 ml/min). In the experiments for oral availability, the duodenum is exposed by a 1 cm long median incision in the upper abdominal region and the test substances are injected into the duodenum from a needle. The substances injected are suspended in tylose (injection volume 1 ml/kg).

TABLE I

Positive inotropic action in vivo on narcotised guinea-pigs after intravenous or intraduodenal administration Increase of dp/dt in percent

| | intravenous application | | intraduodenal application | |
|---|---|---|---|---|
| Substance | Dose $\mu$g/kg/min | dp/dt (increase %) $x \pm sd(n = 3)$ | Dose mg/kg | dp/dt (increase %) $x \pm sd(n = 3)$ |
| Example 1 | 0.6 | 41.8 ± 13.4 | 3.125 | 56.6 ± 14.9 |
| | 1.2 | 146.4 ± 16.7 | 6.25 | 165.0 ± 10.8 |
| Comparison 1 | 10 | 45.8 ± 4.5 | 3.125 | 54.2 ± 21.4 |
| | | | 6.25 | 123.8 ± 42.6 |
| Comparison 2 | 2.5 | 22.7 ± 11.6 | 6.25 | 33.4 ± 16.7 |
| | 5 | 70.8 ± 12.3 | 12.5 | 93.9 ± 18.5 |
| | 10 | 110.6 ± 9.7 | 25.0 | 192.8 ± 24.6 |
| Comparison 3 | 10 | 33.2 ± 18.7 | 3.125 | 67.3 ± 15.8 |
| | | | 6.25 | 154.8 ± 26.6 |
| Comparison 4 | 5 | 10.8 ± 7.6 | 12.5 | 27.2 ± 12.5 |
| | 10 | 21.4 ± 8.4 | 18.8 | 75.7 ± 18.8 |
| | 20 | 25.7 ± 4.6 | 25.0 | 158.5 ± 43.6 |
| Comparison 5 | 10 | 21.6 ± 13.4 | 3.125 | 22.2 ± 9.7 |
| | | | 6.25 | 69.8 ± 12.4 |
| | | | 12.5 | 211.3 ± 42.9 |
| Comparison 6 | 2.0 | 24.6 ± 9.4 | 3.125 | 62.4 ± 18.2 |
| | | | 6.25 | 131.3 ± 15.4 |

TABLE 2

Chemical structures of the Comparison compounds

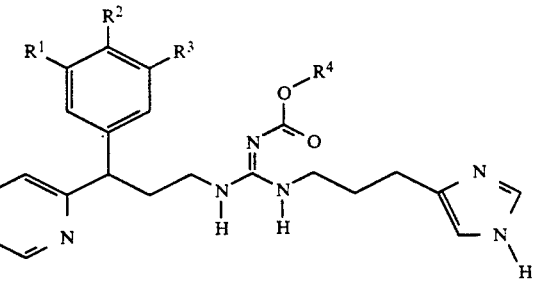

| | R$^1$ | R$^2$ | R$^3$ | R$^4$ |
|---|---|---|---|---|
| Comparison 1[a] | F | F | H | C$_2$H$_5$ |
| Comparison 2[b] | F | H | F | CH$_3$ |
| Comparison 3[c] | F | H | F | C$_2$H$_5$ |
| Comparison 4[d] | F | H | F | n-C$_4$H$_9$ |
| Comparison 5 | F | H | F | t-C$_4$H$_9$ |
| Comparison 6[e] | H | F | H | t-C$_4$H$_9$ |

[a-t]Compounds from DE-OS 37 26 381:
[a]Example 13
[b]Example 24
[c]Example 14
[d]Example 25
[e]Example 16

An important side effect of histamine-H2-agonists is the stimulation of the gastric acid secretion due to the presence of histamine-H$_2$ receptors in the stomach. This limits the usefulness of the compounds for the treatment of cardiac and circulatory diseases since it may cause ulcers of the gastric mucous membrane when given in higher doses or for prolonged periods. It was surprisingly found that the compound of formula (I) produced no significant stimulation of the acid secretion in in vivo experiments on guinea-pigs.

DETERMINATION OF THE ACID SECRETION ON GUINEA-PIGS in vivo

Method

The method of Gosh and Schild (rats) modified for guinea-pigs was used for determining the gastric acid secretion on guinea-pigs in vivo.

Male guinea-pigs having a body weight of about 300 g are narcotised with urethane (2 g/kg i.m.). The abdominal cavity is opened up and a polyethylene tube is introduced through the oesophagus into the stomach. A second tube is introduced into the stomach through the duodenum. This tube has a balloon with a capacity of 10 ml which is blown up with air to reduce the volume of the non-secreting gastric lumen. The bile duct is catheterised to prevent contamination of the gastric juice with bile.

The stomach is perfused with a preheated saline solution (15 ml/10 min) and the perfusate is collected at 10 minute intervals. The quantity of secreted acid in the samples is determined by titration against 0.1 N NaOH, using an automatic titrator (ABU 80 radiometer).

For parenteral application, the test substances are again administered by means of a polyethylene catheter place in the left jugular vein.

TABLE 3

Determination of the gastric acid secretion on narcotised guinea-pigs

| Test substance | Dose μg/kg/min | Increase in acid secretion HCl μeq/ml |
|---|---|---|
| basal secretion | — | 31.8 ± 20.2 |
| Example 1 | 0.3 | 22.6 ± 9.7 |
|  | 0.6 | 83.7 ± 10.1 |
|  | 1.2 | 71.6 ± 10.5 |
|  | 2.4 | 31.2 ± 8.4 |
| Comparison 6 | 2.5 | 122.6 ± 32.3 |
| Comparison A[a] | 0.03 | 12.1 ± 5.0 |
|  | 0.06 | 41.5 ± 10.8 |
|  | 0.12 | 119.2 ± 15.9 |
| Comparison B[b] | 0.015 | 46.8 ± 10.2 |
|  | 0.030 | 53.0 ± 10.3 |
|  | 0.060 | 86.3 ± 11.1 |
|  | 0.125 | 112.1 ± 28.7 |
|  | 0.250 | 121.4 ± 14.8 |
| Impromidine | 0.015 | 27.6 ± 9.5 |
|  | 0.030 | 52.9 ± 21.1 |
|  | 0.060 | 126.2 ± 28.0 |
|  | 0.120 | 116.0 ± 39.3 |

[a] EP-OS 0199 845. Example 133
[b] DE-OS 3631 334. Example 17

The compound according to the invention corresponding to formula I may be prepared by two different process variations:

1.) by the reaction of a compound corresponding to formula II

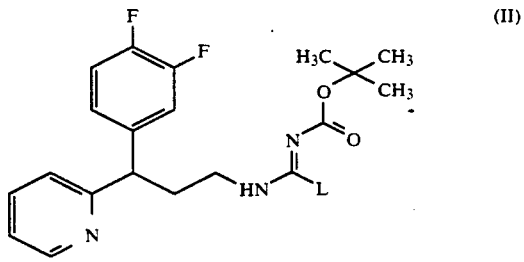

(II)

in which L stands for a $C_1$–$C_4$-alkylthio, a $C_1$–$C_4$-alkoxy, an arylthio- or an aryloxy group, preferably a methylthio or a phenoxy group, with a compound corresponding to formula III

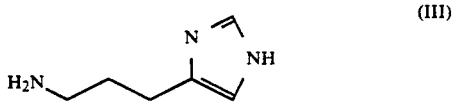

(III)

or

2.) by the reaction of a compound corresponding to formula IV

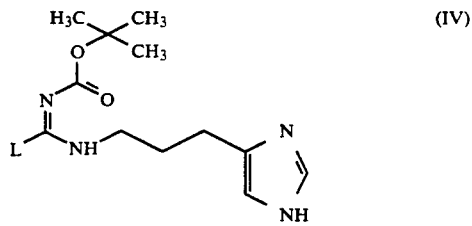

(IV)

in which L has the same meaning as in process variation 1 with a compound corresponding to formula V

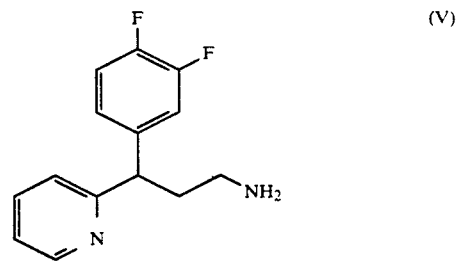

(V)

The reactions are preferably carried out with equimolar quantities and in a polar solvent such as, for example, acetonitrile, dimethylsulphoxide, dimethylformamide or pyridine, preferably in acetonitrile, at temperatures from room temperature to the reflux temperature of the solvent used.

The preparation of the starting compounds of formulae II and IV used in the two process variations is carried out analogously to the methods described in DE-OS 37 26 381.

The compound of formula I obtained by both process variations is isolated and purified by the usual methods, for example by chromatographic methods, recrystallisation, etc.

The compound corresponding to formula I may be converted into one of its physiologically acceptable salts. The invention therefore also covers the physiologically acceptable salts of the compound.

These salts may be formed by known methods, for example with mineral acids such as hydrochloric, hydrobromic or hydriodic acid, phosphoric acid, metaphosphoric acid, nitric acid or sulphuric acid, or with organic acids such as formic acid, acetic acid, propionic acid, phenyl-acetic acid, tartaric acid, citric acid, fumaric acid, methanesulphonic acid, embonic acid, etc.

The compound corresponding to formula I may be converted into one of its physiologically acceptable solvates. The invention therefore also covers the physiologically acceptable solvates of the compound.

These solvates may be prepared, for example, with water, alcohols such as methanol, ethanol, isopropanol or n-butanol, or ketones such as acetone or ethyl methyl ketone.

The solvates may suitably be prepared by dissolving the compound of formula I in the given solvents and crystallising the solvates or by concentration of the solutions by evaporation in a vacuum.

The compounds according to the invention may be formulated for any form of administration. The invention therefore also relates to pharmaceutical compositions containing at least one compound according to the invention for use in human or veterinary medicine. Such pharmaceutical compositions may conventionally be prepared with one or more pharmaceutically acceptable carriers or diluents.

The compounds according to the invention may therefore be formulated for oral, buccal, topical, parenteral or rectal administration.

For oral administration, the pharmaceutical composition may be in the form of, for example, tablets, capsules, powders, solutions, syrups or suspensions which have been prepared by conventional methods using acceptable diluents.

For buccal administration, the pharmaceutical composition may take the form of tablets or sachets formulated in the conventional manner.

The compounds according to the invention may be formulated for parenteral administration by bolus injection or by continuous infusion. Formulations for injection may be prepared in single dose ampoules or in multiple dose containers with added preservative.

The pharmaceutical compositions may assume forms such as suspensions, solutions or emulsions in oily or aqueous carriers and they may contain formulating auxiliaries such as suspending, stabilizing and/or dispersing agents.

Alternatively, the active ingredient may be present in powder form to be reconstituted before use with a suitable carrier such as sterile, pyrogen-free water. The compounds according to the invention may also be formulated for rectal preparations, e.g. suppositories or retention enemas containing, for example, conventional suppository excipients, such as cocoa butter or other glycerides. For topical use, the compounds according to the invention may be formulated in the usual manner as ointments, creams, gels, lotions, powders or sprays.

For oral administration, a suitable daily dose of compounds according to the invention is 1 to 4 doses up to a total of 5 mg to 1 g per day, depending on the patient's condition.

In individual cases it may be necessary to deviate from the quantities indicated, depending on the individual response to the active ingredient and the nature of its formulation and the time and time interval at which administration takes place. Thus there are cases in which less than the minimum quantity indicated above may be sufficient whereas in other cases it may be necessary to exceed the upper limit mentioned.

EXAMPLE 1

$N^1$-[3-(3 4-Difluorophenyl)-3-(2-pyridyl)-propyl]-$N^2$-tert.-butoxycarbonyl-$N^3$-[3-(1H-imidazol-4-yl)propyl]-guanidine

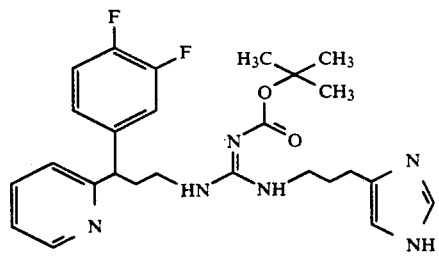

a) $N^1$-[3-(3,4-Difluorophenyl)-3-(2-pyridyl)-propyl]-$N^2$-tert.-butoxycarbonyl-O-phenyl-isourea 6.3 g (20.1 mmol) of N-tert.-butoxycarbonyl-O,O-diphenyl-imidocarbonate are added to 5.0 g (20.1 mmol) of 3-(3,4-difluorophenyl)-3-(2-pyridyl)-propylamine in 50 ml of acetonitrile and the mixture is stirred at room temperature for one hour.

Thin layer chromatographic control of the reaction mixture on DC films polygram SIL G/UV$_{254}$ (Macherey-Nagel) using dichloromethane:methanol 99:1 as eluent shows that the reaction is complete. The product is neither isolated nor purified but used directly for further reactions. $C_{26}H_{27}F_2N_3O_3$ (467.52)

b) $N^1$-[3-(3,4-Difluorophenyl)-3-(2-pyridyl)-propl]-$N^2$-tert.-butoxycarbonyl-$N^3$-[3-(1H-imidazol-4-yl)propyl]guanidine 2.5 g (20.1 mmol) of 3-(1H-imidazol-4-yl)-propylamine are added to the reaction mixture obtained under a). The solution is then boiled under reflux for 13 hours.

After evaporation of the solvent in a water jet vacuum, a yellow oil is obtained, which is chromatographed on 250 g of silica gel 60 (Merck No. 7734) with dichloromethane:methanol 90:10 as solvent.

The fractions having the Rf-value 0.2 are combined and concentrated by evaporation in a vacuum. The colourless oil remaining behind crystallises when stirred up with tert.-butyl methyl ether/ethyl acetate (2:1). 2.8 g (28%) of colourless crystals melting at 94°–95° C. are obtained.

$C_{26}H_{32}F_2N_6O_2$ (498.58)

| $^1$H-NMR-DATA (DMSO-d$_6$, TMS as internal standard) | $\delta =$ 1.37 | (s) | 9H |
|---|---|---|---|
| | 1.74 | (quin) | 2H |
| | 2.15–2.55 | (m) | 4H |
| | 3.0–3.25 | (m) | 4H |
| | 4.19 | (t) | 1H |
| | 6.78 | (s) | 1H |
| | 7.15–7.48 | (m) | 6H. 1H replaceable by D$_2$O |
| | 7.53 | (s) | 1H |
| | 7.70 | (t) | 1H |
| | 8.53 | (d) | 1H |
| | 8.9 | (broad) | 1H. replaceable by D$_2$O ppm. |

We claim:

1. A compound having the formula

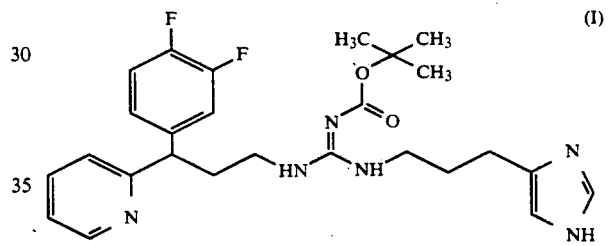

or a physiologically acceptable salt or solvate thereof.

2. A compound according to claim 1, wherein the physiologically acceptable salt is an acid addition salt of an organic orinorganic acid.

3. A pharmaceutical composition of matter, in unit dosage form, for use in the treatment of heart or circulatory disease in a warm-blooded animal, said composition comprising, per dosage unit, a cardiotonically effective amount of a compound having the formula

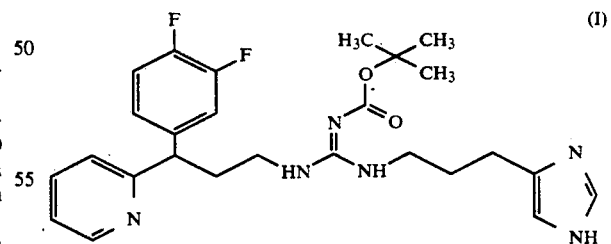

or a physiologically acceptable salt or solvate thereof, and a pharmaceutically acceptable carrier therefor.

4. A pharmaceutical composition according to claim 3, wherein the physiologically acceptable salt is an acid addition salt of an organic or inorganic acid.

5. A pharmaceutical composition according to claim 3, in parenteral dosage form.

6. A pharmaceutical composition according to claim 3, in oral dosage form.

* * * * *